(12) United States Patent
Kobayashi et al.

(10) Patent No.: US 6,506,431 B2
(45) Date of Patent: Jan. 14, 2003

(54) SPORE GERMINATION INHIBITOR AND FOOD CONTAINING THE SAME

(75) Inventors: Katsunori Kobayashi, Kanagawa (JP); Shigeru Yamanaka, Kanagawa (JP); Tomomi Kuwahara, Kanagawa (JP); Hiroshi Miyano, Kanagawa (JP); Kohki Ishikawa, Kanagawa (JP); Ryosuke Fudou, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/781,159

(22) Filed: Feb. 13, 2001

(65) Prior Publication Data

US 2001/0019720 A1 Sep. 6, 2001

(30) Foreign Application Priority Data

Feb. 15, 2000 (JP) .......................................... 2000-036432
Dec. 11, 2000 (JP) .......................................... 2000-375716

(51) Int. Cl.⁷ ........................ C09B 29/036; C12P 17/12; A23L 3/3544
(52) U.S. Cl. ........................ 426/335; 426/654; 435/136; 534/770
(58) Field of Search ................. 426/335, 321, 426/654; 435/121, 128, 135, 136; 534/770

(56) References Cited

U.S. PATENT DOCUMENTS

| | | | | |
|---|---|---|---|---|
| 4,193,979 A | * | 3/1980 | Frank et al. ................ | 424/1.65 |
| 4,361,650 A | * | 11/1982 | Asai et al. .................. | 435/119 |
| 4,658,030 A | * | 4/1987 | Barton et al. ............... | 546/167 |
| 5,298,478 A | | 3/1994 | Yamamoto et al. ......... | 504/115 |
| 5,849,970 A | * | 12/1998 | Fall et al. ..................... | 585/1 |
| 6,010,851 A | | 1/2000 | Mihara et al. ................ | 435/6 |
| 6,015,697 A | | 1/2000 | Mihara et al. | |
| 6,207,435 B1 | | 3/2001 | Mihara et al. | |

FOREIGN PATENT DOCUMENTS

| | | |
|---|---|---|
| JP | XP-002193074 | 9/1967 |
| JP | Xp-002193075 | 3/1976 |

\* cited by examiner

*Primary Examiner*—Keith Hendricks
(74) *Attorney, Agent, or Firm*—Oblon, Spivak, McClelland, Maier & Nuestadt, P.C.

(57) ABSTRACT

The spore germination inhibitor of the invention is 6-carbamoyl-2-pyridine carboxylic acid which is produced by a microorganism of genus Bacillus, such as *Bacillus subtilis,* and can inhibit germination of sporogenous bacteria resulting in the prevention of spoilage and putrefaction of foods, particularly in combination with D-alanine.

17 Claims, No Drawings

SPORE GERMINATION INHIBITOR AND FOOD CONTAINING THE SAME

BACKGROUND OF THE INVENTION

This invention relates to a germination inhibitor of spores, its production and a food using it to improve its keeping quality.

Heretofore, one of the most common methods for sterilizing food in its production is heating, such as pasteurization at a temperature less than about 100° C. or high temperature sterilization at 100° C. or more.

It is possible to sterilize microorganisms in a form of vegetative cell growing in usual circumstances, but bacterial spores exhibiting thermostability cannot be sterilized. While, foods sterilized at a low temperature are occasionally spoiled or putrefied by sporogenous bacteria generated by the germination of survived spores.

Contrarily, bacterial spores having ordinary thermostability can be sterilized by sterilization at a high temperature as well as growing microorganisms. Although high temperature sterilization makes bacterial spores harmless, it simultaneously allows foods to lose their nutrient components and to vary their properties and flavors. Thus, high temperature sterilization degrades food qualities.

In view of food storage, it is considered that the problem of bacterial spores resistant to heat sterilization can be solved by the control of germination of the spores. For examples, all spores are once germinated in advance to be made into a form of vegetative cell, and then sterilized. Alternatively, germination of all spores is inhibited to prohibit multiplication for a long period, or the like.

As to the former method, several spore germinators for *Bacillus subtilis* are known, such as a mixture of L-asparagine, D-glucose, D-fructose and KCl and L-alanine (Yoetsu Hachisuka, "Gahogaku (Sporologies)", Tokaidaigaku Shuppankai, 1988). However, this method is not so effective, because of the presence of spores inferior in germination reactivity remarkably, different spore germinators for the type of bacteria, or the like.

As to the latter method, there are known spore germination inhibitors for *Bacillus subtilis*, such as D-amino acids including D-alanine (Y. Yasuda & K. Tochikubo: Microbiol. Immunol., 29, 229 (1985)), various alcohols (Y. Yasuda—Yasaki, et al.: J. Bacteriol., 136, 484 (1979)), various fatty acids, etc. (T. Yasuda, et al.: J. Med. Chem., 25, 315 (1982), $HgCl_2$, and so on, but this method is also not so effective, because of insufficient inhibition, remarkably high toxicity, or the like.

SUMMARY OF THE INVENTION

An object of the invention is to provide a spore germination inhibitor, which renders foods, etc. contaminated with thermostable bacterial spores as well as general bacteria, preservable by the sterilization in the degree of pasteurization without conventional high temperature sterilization which degrades food qualities.

Another object of the invention is to provide a method of producing the spore germination inhibitor.

Still another object of the invention is to provide a food using the spore germination inhibitor.

The inventors investigated eagerly in order to achieve the above objects, and concluded that the most preferable means is to use a natural germination inhibitor for bacterial spores. Thereupon, they further investigated in order to find a substance which inhibits germination of bacterial spores effectively, and as a result, they have found that bacteria belonging to genus Bacillus which are sporegenous, such as *Bacillus subtilis*, produce a spore germination-inhibiting substance which has a great spore germination-inhibiting ability and no toxicity problem, that the germination-inhibiting substance is 6-carbamoyl-2-pyridine carboxylic acid, and that its salts and derivatives also have germination-inhibiting action, to complete the invention.

Thus, the present invention relates to a spore germination inhibitor which comprises 6-carbamoyl-2-pyridine carboxylic acid or a salt or derivative thereof, a food containing it, and a method of producing 6-carbamoyl-2-pyridine carboxylic acid which comprises culturing a bacterium belonging to genus Bacillus, and collecting 6-carbamoyl-2-pyridine carboxylic acid from the culture medium.

DETAILES DESCRIPTION OF THE INVENTION

The microorganisms belonging to genus Bacillus, which produce 6-carbamoyl-2-pyridine carboxylic acid (CPC), are not especially limited, and include *Bacillus subtilis* ATCC 33234, FERM BP-5325, FERM BP-5367, etc.

The form of culture may be either liquid culture or solid culture, and submerged culture with aeration is preferred in the industrial viewpoint. Nutrients in a culture medium may be conventional carbon source, nitrogen source, inorganic salts and the other minor nutrients used for culture of a microorganism. Culture is carried out under aerobic conditions at a temperature capable of growing the bacterium employed in the invention to produce CPC, preferably in the range from 30 to 40° C., for a period from 5 hours to 2 days.

The spore germination inhibitor can be separated from a cultured matter by a conventional method for purifying a material, such as solvent extraction, various chromatographys, gel filtration or the like.

6-carbamoyl-2-pyridine carboxylic acid (CPC) which is the spore germination inhibitor of the invention has the following formula and properties.

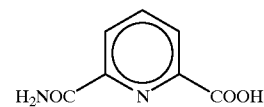

White powder

Soluble in water, particularly alkaline water, and organic solvent, such as pyridine and DMSO The subject bacterial spores, which are inhibited by the spore gemination-inhibiting substance of the invention, are spores of sporogenous bacteria found in usual contamination of foods, such as *Bacillus subtilis, Bacillus cereus, Clostridium perfringens* and the like.

CPC used in the invention is not limited to the CPC produced by the aforementioned bacteria, and includes CPC produced by conversion with an enzyme or through chemical synthesis.

The salt of CPC may be any salt containing Na, K or the like or Cl, $NO_3$ or the like.

The derivative of CPC includes CPC of which —$CONH_2$ at 6-position is substituted by a functional group containing an amide bond represented by —CONHR. For example, effective derivatives are containing —CONHR wherein R is —$NH_2$ or —NHR is an amino acid residue. Still effective derivatives are carboxyl group and/or carbamoyl group are transferred to any other position from 2-position to 6-position.

The salts and derivatives of CPC can be produced by a conventional method.

A suitable blending amount of CPC, its salt or derivative is 0.01 to 5 wt. % of a food to be stored, preferably 0.05 to 2 wt. %. CPC, its salt or derivative can be used as a germination inhibitor as is, but a known substance to inhibit germination, such as D-alanine, various alcohols or various fatty acids, may be combined therewith. Furthermore, a known fungicide, bacteriocide or preservative may be combined.

Spore germination-inhibiting effects are exhibited remarkably by combining D-alanine with CPC or its salt or derivative. Although several germination inducing substances, which stimulate germination of spores of *Bacillus subtilis*, are known, such as L-alanine, in addition to a mixture of L-asparagine, D-glucose, D-fructose and KCl (AGFK system), it is difficult to specify which component stimulates germination in the presence of many nutrients, such as in food. Therefore, as mentioned previously, it is expected that, although germination of spores in food mainly belonging to AGFK system can be inhibited by CPC alone, the inhibition to germination may be not complete by CPC in the presence of sufficient nutrients. Then, the inventors examined the effects by the combination with D-alanine, which is another spore germination inhibitor, and found its remarkable synergistic effects.

In the case of the combination of D-alanine with CPC, a suitable blending amount of CPC, its salt or derivative is 0.01 to 5 wt. % of a food to be stored, preferably 0.05 to 2 wt. % as mentioned previously. A suitable blending amount of D-alanine depends on the L-alanine content of the food to be stored, and is 30 to 200 wt. % of the L-alanine in the food, preferably 40 to 100 wt. %. In general, the blending amount of D-alanine is in the range from 0.01 to 5 wt. % of the food to be stored.

In an embodiment for practicing germination inhibition, CPC, its salt or derivative is added to a food to be stored, and subjected to asteurizaiton to sterilize microorganisms in a vegetative cell state other than spores and to keep the spores in a state of not germinated. The foods treated as above can be inhibited from spoilage and putrefaction by sporogenous bacteria for a long period by a simple storage, compared with foods subjected to only pasteurization. In another embodiment, it is also effective to add CPC, its salt or derivative to food after subjected to pasteurization. In another embodiment, it is also effective to inhibit germination of spores in a state of death or growth inhibition of microorganisms in vegetative cell state other than spores, by a combination of a bacteriocide, fungicide, bacteriostat or fungistat with CPC, its salt or derivative.

Furthermore, it is also effective to apply or spray CPC, its salt or derivative onto the surface of food or the surface of a packaging material which package a food.

EXAMPLES

Example 1

Production and Purification of CPC

*Bacillus subtilis* ATCC 33234 was cultured to obtain a culture solution having a sufficient germination-inhibitory activity. Using a Schaeffer's liquid medium, cultivation was carried out at 37° C. by shaking culture. The composition of the Schaeffer's medium is 8 g/l Bacto-nutrient broth, 1 g/l KCl, 0.12 g/l $MgSO_4.7H_2O$, 1 mM $CaCl_2$, 10 $\mu$M $MnCl_2$, 1 $\mu$M $FeSO_4$, pH 7.0.

50 ml culture was carried out overnight as a seed culture, and using 25 ml of the culture solution as the seed, 500 ml culture was carried out. After multiplication entered stationary state, cultivation was finished after 24 hours. The culture solution was centrifuged to separate culture supernatant having germination-inhibitory activity.

The germination-inhibitory activity was measured as follows: ½ volume of a sample was allowed to react with ½ volume of spore suspension (0.2 mg/ml *Bacillus subtilis* spores, 40 mM Tris HCl, pH 7.5) containing germinator (20 mM L-asparagine, 2 mM D-glucose, 2 mM D-fructose, 20 mM KCl) at 37° C. The spores gradually darkened with germination increase, and turbidity of the suspension decreased. Thereupon, the turbidity of the spore suspension was measured at 600 nm using a spectrophotometer, and a germination rate was determined by calculating the rate of decrease of turbidity.

The culture supernatant having germination-inhibitory activity was adjusted to pH 2 by HCl, and solvent extraction was carried out with an equal volume of butanol to recover the active component. The butanol extract solution was evaporated to dryness, and dissolved in 1/20 volume of a Tris buffer solution (100 mM Tris.HCl, pH 8).

Subsequently, non-polar solid phase extraction was carried out using octadecyl group-bonded silica (ODS) as follows: The above solution was adjusted to pH 2 by HCl, and an adequate volume thereof was fed to an ODS column to adsorb the substance having germination-inhibitory activity. Then, the column was washed with 5 times the volume of 0.1% trifluoroacetic acid (TFA) as much as the column volume, and the inhibitory active component was eluted with 5 times the volume of 0.1% TFA/20% acetonitrile to recover it.

Reverse phase HPLC was carried out using ODS as follows: The above activity fractions were evaporated to dryness, and dissolved in an adequate volume of a Tris buffer solution. The solution was adjusted to pH 2 by HCl, and an adequate volume thereof was fed to an ODS column previously equilibrated with 0.1% TFA, and eluted by acetonitrile with varying linearly its concentration from 0% to 30%. From elute fractions, peak fractions wherein the inhibitory activity was detected were recovered.

Then, ion exchange HPLC was carried out as follows: The above activity fractions were evaporated to dryness, and dissolved in an adequate volume of Tris buffer solution (20 mM Tris.HCl, pH 8). After adjusting the pH of the solution to 8 by a sodium hydroxide solution, an adequate volume thereof was fed to an anion exchange column TSK gel Super Q-5PW (Toso Co., Ltd.) previously equilibrated with the same Tris buffer solution to adsorb the active component. Then, the active component was eluted by sodium chloride solution with varying linearly its concentration from 0 M to 1 M, and peak fractions wherein the inhibitory activity was detected were recovered.

Finally, the reverse phase HPLC was carried out using ODS similar to aforementioned process, and the activity fractions were evaporated to dryness. The dried matter thus obtained was made the final purified product. In order to determine the structure of the final purified product, various instrumental analyses were carried out, and found that the molecular weight was 166 by FABMS, and the chemical formula was $C_7H_6N_2O_3$ by High MS/NMR. Furthermore, by the analyses of NMR and X-ray crystal diffractometry, it was determined that the spore germination inhibitor is CPC.

Example 2

Spore Germination-Inhibitory Effects by CPC

In order to examine the germination-inhibitory effects of CPC, the following tests were conducted.

Test Group 1: Germination not occurs

Spore suspension containing 0.1 mg/ml *Bacillus subtilis* spores, 20 mM Tris.HCl, pH 7.5.

Test Group 2: Germination occurs enough

Spore suspension as above further containing 10 mM L-asparagine, 1 mM D-glucose, 1 mM D-fructose and 10 mM KCl as germinator.

Test Group 3: CPC added

Spore suspension as above containing the germination (Test Group 2) and further containing 1 mg/ml CPC.

The above spore suspensions were allowed to react at 37° C. for 2 hours, and spore germination conditions were examined.

The turbidity of each test group after 2 hours was measured at 600 nm using a spectrophotometer. In the test group 2, the turbidity of the spore suspension was decreased remarkably compared with the start of the reaction, and sufficient germination of spores was found. In the test group 1, the turbidity of the spore suspension was scarcely varied from the start of the reaction, and germination was not observed. In the test group 3 containing CPC, the turbidity of the spore suspension was not decreased, and germination was not observed, similar to the test group 1.

When the spore suspensions of respective test groups were observed by a phase-contrast microscope, it was found that, in the test group 2, almost all of spores were darkened with losing light refractivity, i.e. were germinated. Conversely, in the test groups 1 and 3, no darkened spore was observed, and all spores had light refractivity, i.e. germination of spores was not recognized. From the above results, it was confirmed that CPC has germination-inhibitory effects on spores.

Example 3

Improvement in Germination Inhibition by Combination of CPC and D-Alanine

In the presence of various nutrients, such as food, it is difficult to specify which component stimulates germination. Therefore, it is expected that germination cannot be inhibited completely by CPC alone in the presence of sufficient nutrients.

Thereupon, in order to examine germination-inhibitory effects by the combination of CPC and D-alanine which is a known germination-inhibitory substance, the following test groups were prepared.

Test Group 1: Germination not occurs

Spore suspension containing 0.1 mg/ml *Bacillus subtilis* spores, 20 mM Tris.HCl, pH 7.5.

Test Group 2: Germination occurs enough

Spore suspension containing 0.1 mg/ml *Bacillus subtilis*, 25 g/l Bacto-LB broth, Miller (DIFCO) as sufficient nutrients, and 10 mM L-asparagine, 1 mM D-glucose, 1 mM D-fructose and 10 mM KCl (AGFK system) as germinator.

Test Group 3: CPC added

Spore suspension as above containing the sufficient nutrients (Test Group 2) and further containing 1 mg/ml CPC.

Test group 4: D-Alanine added

Spore suspension as above containing the sufficient nutrients (Test Group 2) and further containing 1 mg/ml D-alanine.

Test Group 5: CPC and D-alanine added

Spore suspension as above containing the sufficient nutrients (Test Group 2) and further containing 1 mg/ml CPC and 1 mg/ml D-alanine.

The above spore suspensions were allowed to react at 37° C. for 2 hours, and spore germination conditions were examined.

The variation of the turbidity of each test group was measured through the above reaction at 600 nm using a spectrophotometer. In the test group 1, the turbidity of the spore suspension was scarcely varied from the start of the reaction, and germination was not observed. In the test group 2, the turbidity of the spore suspension was initially decreased remarkably, and then turned to increase. After 2 hours, the turbidity became the same turbidity as the initial one, and growth subsequest to the germination (vegetative growth) was observed. In the test groups 3 and 4 containing CPC or D-alanine, the turbidity of the spore suspension was initially decreased, and then turned to increase, and growth subsequent to the germination was observed, similar to the test group 2. On the other hand, in the test group 5 containing CPC and D-alanine, decrease of the turbidity was not observed, similar to the test group 1.

Each inhibition rate was calculated based on the variation of $OD_{600}$ value for 30 minutes from the start of measurement wherein the germination inhibition rate in the test group 1 is assigned 100% and that in the test group 2 is assigned 0%. As a result, the inhibition rates were 9% for the test group 3, 16% for the test group 4, and 90% for the test group 5, respectively.

From the above results, it can be seen that, germination in sufficient nutrition conditions, which cannot be inhibited sufficiently by CPC or D-alanine alone, can be inhibited by a combination thereof.

According to the invention, spoe germination of sporogenous bacteria in foods contaminated or remaining in their production processes can be inhibited or prohibited by adding CPC. Therefore, spoilage and putrefaction of foods can be prevented, and stored easily without high temperature sterilization.

What is claimed is:

1. A spore germination inhibitor which comprises 6-carbamoyl-2-pyridine carboxylic acid or a salt or derivative thereof, and D-alanine.

2. The spore germination inhibitor of claim 1, wherein the salt is a member selected from the group consisting of Na salt, K salt, Cl salt and $No_3$ salt.

3. The spore germination inhibitor of claim 1, wherein the derivative contain —CONHR wherein R is —$NH_2$ or —NHR is an amino acid residue, or wherein the carboxyl group or carbamoyl group in the 6-carbamoyl-2-pyridine carboxylic acid is transferred to another position.

4. A food composition which comprises a food product, 6-carbamoyl-2-pyridine carboxylic acid or a salt or derivative thereof, and D-alanine.

5. The food composition of claim 4, wherein 6-carbamoyl-2-pyridine carboxylic acid or a salt or derivative thereof is contained in an amount of 0.01 to 5 wt. %.

6. The food composition of claim 4, wherein 6-carbamoyl-2-pyridine carboxylic acid or a salt or derivative thereof is contained in an amount of 0.01 to 5 wt. % and D-alanine is contained in an amount of 30 to 200 wt. % of L-alanine in the food.

7. A method of producing 6-carbamoyl-2-pyridine carboxylic acid which comprises culturing a bacterium which belongs to genus Bacillus and is capable of producing 6-carbamoyl-2-pyridine carboxylic acid, and isolating 6-carbamoyl-2-pyridine carboxylic acid accumulated in the culture medium.

8. The method of claim 7, wherein said bacterium is *Bacillus subtilis*.

9. The method of claim 8, wherein said *Bacillus subtilis* is *Bacillus subtilis* ATCC 33234, *Bacillus subtilius* BP-5325, and *Bacillus subtilis* BP-5367.

10. The germination inhibitor of claim 1, which comprises (a) D-alanine and (b) a sodium salt of 6-carbamoyl-2-pyridine carboxylic acid.

11. The germination inhibitor of claim 1, which comprises (a) D-alanine and (b) a potassium salt of 6-carbamoyl-2-pyridine carboxylic acid.

12. The germination inhibitor of claim 1, which comprises (a) D-alanine and (b) a Cl salt of 6-carbamoyl-2-pyridine carboxylic acid.

13. The germination inhibitor of claim 1, which comprises (a) D-alanine and (b) a nitrate salt of 6-carbamoyl-2-pyridine carboxylic acid.

14. The food composition of claim 4, which comprises (a) D-alanine, and (b) a sodium salt of 6-carbamoyl-2-pyridine carboxylic acid, and (c) a food product.

15. The food composition of claim 4, which comprises (a) D-alanine, and (b) a potassium salt of 6-carbamoyl-2-pyridine carboxylic acid, and (c) a food product.

16. The food composition of claim 4, which comprises (a) D-alanine, and (b) a Cl salt of 6-carbamoyl-2-pyridine carboxylic acid, and (c) a food product.

17. The food composition of claim 4, which comprises (a) D-alanine, and (b) a nitrate salt of 6-carbamoyl-2-pyridine carboxylic acid, and (c) a food product.

* * * * *